(12) United States Patent
Bogatu et al.

(10) Patent No.: US 6,614,878 B2
(45) Date of Patent: Sep. 2, 2003

(54) X-RAY FILTER SYSTEM FOR MEDICAL IMAGING CONTRAST ENHANCEMENT

(75) Inventors: Ioan Niculae Bogatu, San Diego, CA (US); Jin-Soo Kim, San Diego, CA (US)

(73) Assignee: Fartech, Inc., San Diego, CA (US)

( * ) Notice: Subject to any disclaimer, the term of this patent is extended or adjusted under 35 U.S.C. 154(b) by 25 days.

(21) Appl. No.: 09/767,992

(22) Filed: Jan. 23, 2001

(65) Prior Publication Data

US 2003/0103598 A1 Jun. 5, 2003

(51) Int. Cl.[7] .................................................. G21K 3/00
(52) U.S. Cl. ........................ 378/158; 378/62; 378/156; 378/157
(58) Field of Search ........................... 378/51, 66, 157, 378/158, 159, 160, 161, 156, 62

(56) References Cited

U.S. PATENT DOCUMENTS

| | | | |
|---|---|---|---|
| 4,254,778 A | | 3/1981 | Clow |
| 4,296,378 A | | 10/1981 | King |
| 4,498,048 A | | 2/1985 | Lee |
| 4,656,425 A | | 4/1987 | Bendel |
| 4,766,378 A | | 8/1988 | Danby |
| 4,829,252 A | | 5/1989 | Kaufman |
| 4,870,363 A | | 9/1989 | Yassine |
| 4,887,604 A | * | 12/1989 | Shefer et al. ................ 600/431 |
| 5,081,660 A | * | 1/1992 | Fujisaki ....................... 378/156 |
| 5,099,208 A | | 3/1992 | Fitzpatrick |
| 5,184,074 A | | 2/1993 | Arakawa |
| 5,204,888 A | * | 4/1993 | Tamegai et al. ............... 378/53 |
| 5,755,666 A | | 5/1998 | Bornert |
| 6,061,426 A | | 5/2000 | Linders |
| 6,094,468 A | | 7/2000 | Wilting |
| 6,226,352 B1 | * | 5/2001 | Salb ........................... 378/143 |
| 6,289,074 B1 | * | 9/2001 | Arai et al. ..................... 378/4 |

OTHER PUBLICATIONS

Zeman et al., Contrast Agent Choice for Intravenous Coronary Angiography, 1990, Nuclear Instruments and Methods in Physics Research A291, 67–93, North–Holland.

Dilmanian et al., CT with Monochromatic Synchrotron X Rays and Its Potential in Clinical Research, 1997, SPIE vol. 3149.

* cited by examiner

*Primary Examiner*—Drew A. Dunn
*Assistant Examiner*—Courtney Thomas
(74) *Attorney, Agent, or Firm*—Nydegger & Associates

(57) ABSTRACT

A system for creating an image of the internal features of an object includes an X-ray source and detector array positioned to interpose the object between the X-ray source and the detector array. An X-ray beam is passed through the object along a first path. While passing through the object, the beam is successively filtered four times, each time with a different filter. The successive filtration of the beam results in the production of four electrical signals by the detector which are processed to create an image signal for the path. The process is repeated for a plurality of paths through the object and the resulting image signals are combined using traditional computer tomography techniques to produce an image of the object.

32 Claims, 5 Drawing Sheets

X-RAY FILTER SYSTEM FOR MEDICAL IMAGING CONTRAST ENHANCEMENT

FIELD OF THE INVENTION

The present invention pertains generally to devices and methods for imaging the internal features of an object. More particularly, the present invention pertains to improved devices and methods for imaging the internal features of an object while using a conventional broadband X-ray source. The present invention is particularly, but not exclusively, useful for producing an enhanced-contrast image of the internal features of an object by using filtered X-ray radiation.

BACKGROUND OF THE INVENTION

The ability to image the internal features of an object is important in many applications. Two examples include medical diagnosis and the non-destructive testing of structural components to detect configuration or discover internal flaws. In all applications, it is desirable to produce an image having high contrast and spatial resolution. Radiation within the X-ray spectrum is often used to image internal features because of the ability of X-ray radiation to penetrate matter and because different matter absorbs X-ray radiation at different rates. Typically, a conventional X-ray source produces an emission of X-ray radiation having a broad range of energies. In conventional imaging applications, these X-rays are directed through the object for subsequent capture by a film or detector. The imaging films and detectors used are responsive to the intensity of the radiation received, and thus are able to produce an image of the internal features of the object when those internal features have differing absorption characteristics.

To enhance the contrast and spatial resolution of an image, contrast agents are often used. Specifically, these agents include chemical elements that have absorption rates that are significantly different than the constituents of the object to be imaged. For example, iodine can be administered within the body as a contrast agent. Once administered, the iodine is selectively absorbed by certain tissues or is present within the blood vessels. Subsequently, when an X-ray image is formed, areas of the body with large amounts of iodine will absorb relatively greater amounts of X-ray radiation than areas of the body without iodine. Thus, contrast agents can be used with good efficacy to increase both the contrast and the spatial resolution of the image.

FIG. 1 shows the variation of absorption coefficient with radiation energy for a typical chemical element. In simple terms, the absorption coefficient decreases as the energy increases until an energy is reached that is sufficient to knock a K-shell electron from it's orbit. At this energy, $E_{K\text{-}EDGE}$, the value of the absorption coefficient jumps. For purposes of the present disclosure, the term $K_{EDGE}$ is used to denote the energy at which the jump in absorption coefficient occurs. Continuing with FIG. 1, it can be seen that further increases in energy again result in a gradual decrease in absorption coefficient.

The present invention recognizes that the variation in absorption coefficient near $K_{EDGE}$ can be utilized to increase image contrast. Specifically, the present invention recognizes that image contrast can be increased by first introducing a contrast agent having a known $K_{EDGE}$ into the object. Next, a first image can be formed using monochromatic radiation having an energy just less than $K_{EDGE}$ for the contrast agent (such as radiation having an energy, $E_1$, in FIG. 1) and a second image formed using monochromatic radiation having an energy just greater than $K_{EDGE}$ for the contrast agent (such as radiation having an energy, $E_2$, in FIG. 1). When this is done, the resulting two images can be compared (subtracted) to produce a high contrast image of the internal features of the object.

One way to produce the monochromatic X-ray radiation needed to conduct the above described subtraction method is to use a crystal monochromator. Unfortunately, when a crystal monochromator is used in conjunction with a conventional X-ray source, the intensity of the resulting monochromatic radiation is so reduced that the radiation is insufficient for almost all practical imaging uses. One way to produce monochromatic radiation at a suitable intensity for imaging is to pass the high intensity radiation from a synchrotron source through a double crystal monochromator. As can be expected, producing radiation with a synchrotron source is very expensive. Further, the beam produced by the synchrotron source/double crystal monochromator is fixed in direction and, consequently, cannot be rapidly moved as required in a typical tomographic scan.

In light of the above, it is an object of the present invention to provide devices and methods suitable for the purposes of producing a digital image signal that is substantially equivalent to an image signal obtained by passing quasi-monochromatic radiation (i.e. radiation having a narrow energy band) through an object. It is another object of the present invention to provide devices and methods for producing images of the internal features of an object having enhanced contrast and high spatial resolution. It is yet another object of the present invention to provide devices and methods for use in conjunction with standard computer tomography or angiography equipment to enhance the contrast and increase the spatial resolution of the images produced. It is yet another object of the present invention to provide devices and methods for enhancing image contrast and increasing spatial resolution that can be used with a variety of different contrast agents. Yet another object of the present invention is to provide an X-ray Filter System For Medical Imaging Contrast Enhancement which is easy to use, relatively simple to manufacture, and comparatively cost effective.

SUMMARY OF THE PREFERRED EMBODIMENTS

The present invention is directed to a system for creating an image of the internal features of an object. Specifically, the present invention is directed at imaging an object that contains a contrast agent. For the present invention, the system includes an X-ray source configured to produce a spectrum of X-ray radiation. An optional collimator may be provided to collimate the radiation emitted from the X-ray source into one or more beams. As such, each beam emanates from the X-ray source in a slightly different direction, and consequently, along a separate path. For the present invention, the X-ray source is oriented relative to the object to direct all such paths towards the object. Further, a mechanism is provided to move the X-ray source relative to the object to cause each radiation beam emanating from the X-ray source to successively travel on different paths through the object. For example, the X-ray source can be slideably mounted on a circular track that extends around the object.

A detector array is positioned on the opposite side of the object to interpose the object between the X-ray source and the detector array. Preferably, the detector array includes a plurality of detectors, one detector for each beam that emanates from the X-ray source/collimator assembly.

Further, a mechanism can be provided to move the detector array as the X-ray source is moved. Specifically, the detector array can be moved to allow each detector to track a single X-ray beam, as that X-ray beam travels on successive paths through the object. In response to the receipt of an X-ray beam, the detector produces an electrical signal that is proportional to the intensity of the radiation received.

An important aspect of the present invention is that the X-ray radiation is filtered between the X-ray source and the detectors. Specifically, for each X-ray beam on each path, the beam is successively filtered four times, each time with a different filter. Each time the beam is moved to a new path, the beam is once again filtered four times. Each time the beam is successively filtered four times, four different electrical signals are produced by a detector.

For the present invention, these four electrical signals can be manipulated by a processor to produce an image signal for the path. Once an image signal is established for each desired path, conventional tomography techniques can be used to combine all the image signals (one image. signal for each path) into a composite image that reveals the internal features of the object.

For the present invention, a filter set having four different filters is used to successively filter each beam on each path. In accordance with the present invention, a unique filter set is designed for use with a specific contrast agent that is prescribed for introduction into the object. Specifically, the chemical constituents and thickness of each filter are determined with reference to the specific contrast agent that is being used. For a contrast agent with a chemical element having a $K_{EDGE, \ CONTRAST \ AGENT}$, a filter set is used having a first filter with a chemical element having a $K_{EDGE}$ that is greater than $K_{EDGE, \ CONTRAST \ AGENT}$, a second filter with a chemical element having a $K_{EDGE}$ that is greater than or equal to $K_{EDGE, \ CONTRAST \ AGENT}$, a third filter with a chemical element having a $K_{EDGE}$ that is less than or equal to $K_{EDGE, \ CONTRAST \ AGENT}$, and a fourth filter with a chemical element having a $K_{EDGE}$ that is less than $K_{EDGE, \ CONTRAST \ AGENT}$.

A mechanism is provided to successively interpose each filter of the filter set between the X-ray source and the object to thereby allow the successive filtration of the beams emanating from the source. For example, the filter set can be mounted on either an oscillating frame or a rotating wheel. For the embodiment with the wheel, all four filters are mounted on the wheel, and a motor is provided to rotate the wheel about the wheel's axis. The wheel and motor can be attached to the X-ray source to allow the wheel, filters and motor to travel with the X-ray source/collimator assembly as the assembly moves with respect to the object.

In operation, first the contrast agent is introduced into the object, and the object is placed between the X-ray source and the detector array. Next, the X-ray source is located at a first position and activated to produce one or more beams travelling through the object on a first set of paths (one path for each beam). Next, the wheel containing the filters is rotated to successively interpose each of the four filters between the X-ray source/collimator assembly and the object to filter each of the beams with each of the four filters. This results in the production of four intensity-proportional signals by a detector for each beam.

For the present invention, these four signals can be manipulated either on-line or off-line by a processor to produce an image signal for the path. Specifically, the processor subtracts the digital signal produced by the detector with the second filter interposed along the path from the digital signal produced by the detector with the first filter interposed along the path. The result of this is a first intermediary difference signal. This first intermediary difference signal simulates the image signal that would be obtained if a quasi-monochromatic beam having an average energy slightly below $K_{EDGE, \ CONTRAST \ AGENT}$ were to be passed through the object along the path. Similarly, the processor subtracts the digital signal produced by the detector with the fourth filter interposed along the path from the digital signal produced by the detector with the third filter interposed along the path. The result of this is a second intermediary difference signal. This second intermediary difference signal simulates the image signal that would be obtained if a quasi-monochromatic beam having an average energy slightly above $K_{EDGE, \ CONTRAST \ AGENT}$ were to be passed through the object along the path. Next, the processor is programmed to subtract the second intermediary difference signal from the first intermediary difference signal to produce the final image signal for the path.

Once image signals are obtained for the first set of paths, the X-ray source/collimator assembly can be moved to a second position to cause the beams emanating from the assembly to travel along a new set of paths. While the X-ray source/collimator assembly is at the second position, the wheel is again rotated to successively interpose each of the four filters between the X-ray source/collimator assembly and the object to again filter each of the beams with each of the four filters. Again, four intensity-proportional signals are produced by a detector for each beam. For the present invention, these four signals can be manipulated by a processor as described above to produce an image signal for each new path. This process of moving the X-ray source/collimator assembly and producing an image signal for each new path can be repeated as desired. Further, it is to be appreciated that the X-ray source/collimator assembly can be moved continuously around the object. When this technique is used, the wheel containing the filters can be rotated continuously as the X-ray source moves. By rotating the wheel very rapidly, each beam can be filtered four times before significant movement of the beam occurs. Thus, in effect, each beam remains on a single path while the successive filtration takes place. Once an image signal is produced for all paths of interest, conventional tomography techniques can be used to combine all the image signals (one image signal for each path) into a composite image that shows the internal features of the object.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 2:
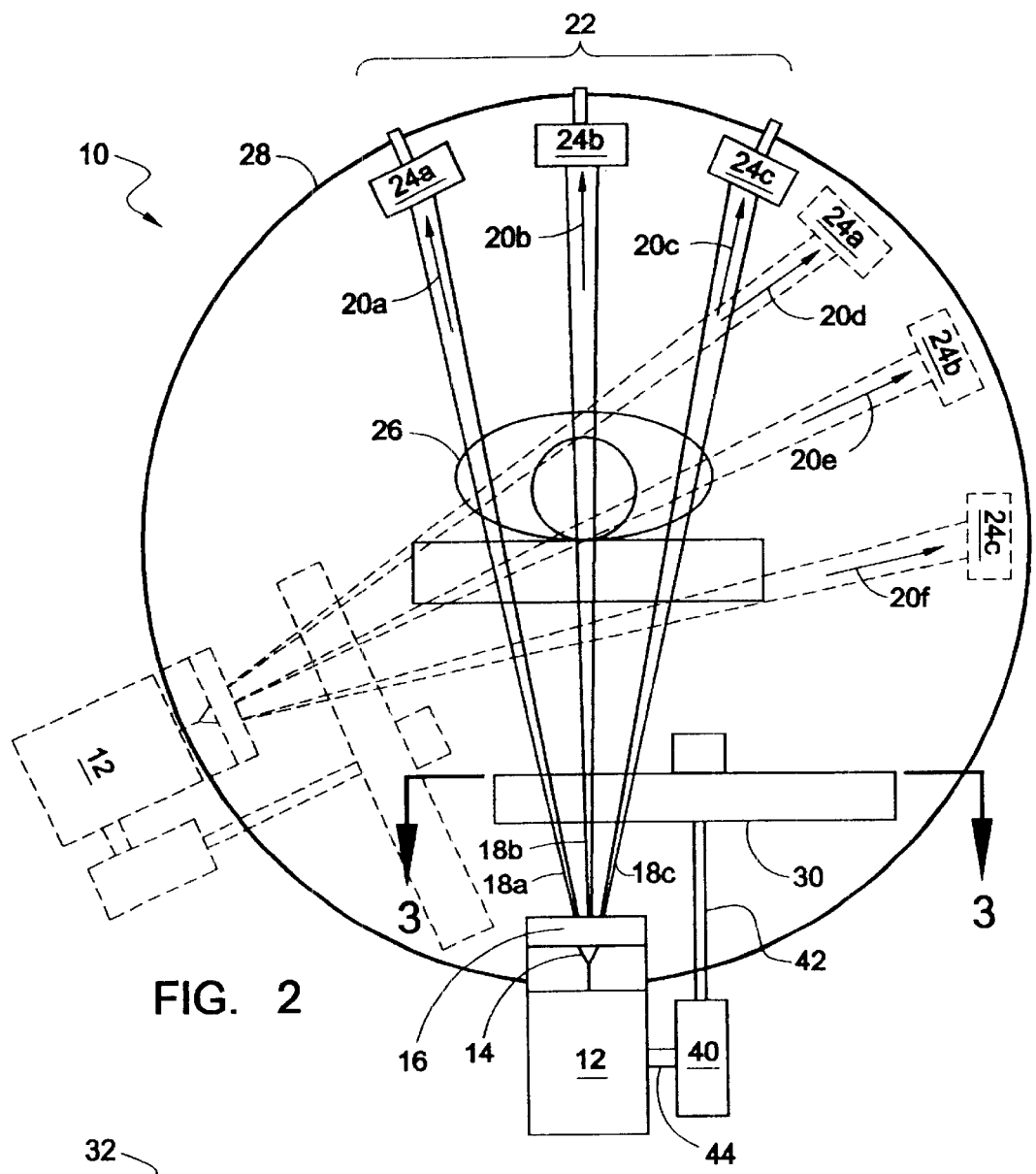
FIG. 2 is a plan view of a system in accordance with the present invention shown imaging a portion of a human body.

Referring initially to FIG. 2, an imaging system in accordance with the present invention is shown and generally designated 10. As shown in FIG. 2, the system 10 includes an X-ray source 12 configured to produce a spectrum of X-ray radiation 14. An optional collimator 16 may be provided to collimate the radiation 14 emitted from the X-ray source 12 into one or more beams 18a–c. As such, each beam 18 emanates from the X-ray source 12 in a slightly different direction, and consequently, along a separate path 20a–c. It is to be appreciated that the use of three beams 18 is merely exemplary and that as many beams 18 as desired may be used in accordance with the present invention. In detail, as shown in FIG. 2, beam 18a initially travels substantially along path 20a, beam 18b initially travels substantially along path 20b and beam 18c initially travels substantially along path 20c.

Referring still to FIG. 2, a detector array 22 is shown positioned to receive the beams 18 from the source 12. Specifically, the detector array 22 is shown having three detectors 24a–c, with detector 24a positioned to receive beam 18a, detector 24b positioned to receive beam 18b and detector 24c positioned to receive beam 18c. For the present invention, an object 26 can be interposed between the X-ray source 12 and the detector array 22 to thereby allow the beams 18 to be modified by passing through the object 26 before reaching the detectors 24. In accordance with the present invention, the detectors 24 can be any type of detector known in the pertinent art capable of receiving radiation and producing an electrical signal that is proportional to the intensity of the radiation received. For example, the detectors 24 can be solid state detectors (separate or having a charge couple detector structure), gas-filled detectors or scintillators with photo-multipliers. Preferably, each detector 24 is a small-area X-ray detector. For the present invention, the output of each detector 24 is electrically wired to a computer (not shown) to allow the signals generated by the detectors 24 to be processed.

Also shown in FIG. 2, the X-ray source 12 can be slideably mounted on a circular track 28 that extends around the object 26. Additionally, as shown, each detector 24 or the entire detector array 22 can be slideably mounted on the track 28. As such, the X-ray source 12 and detectors 24 can be moved either continuously or incrementally around the track 28 and relative to the object 26. The dashed lines in FIG. 2 show an exemplary second position for the X-ray source 12 and detectors 24. By moving the X-ray source 12, each radiation beam 18 emanating from the X-ray source 12 can be caused to successively travel on different paths 20 through the object 26. For example, as shown in FIG. 2, when X-ray source 12 is in the initial position represented by the solid lines, beam 18a travels substantially along path 20a, and when X-ray source 12 is moved to a second position represented by dashed lines, beam 18a travels substantially along path 20d. Similarly, beam 18b travels substantially along path 20e and beam 18c travels substantially along path 20f when the X-ray source 12 is in the position indicated by dashed lines.

Accordingly, the detector array 22 can be moved in conjunction with the X-ray source 12 to allow each detector 24 to track a single X-ray beam 18, as that X-ray beam 18 travels on successive paths 20 through the object 26.

An important aspect of the present invention is that the X-ray radiation 14 is filtered between the X-ray source 12 and the detectors 24. By cross-referencing FIGS. 2 and 3, it can be seen that a wheel 30 having attached filters 32, 34, 36 and 38 can be used to successively filter each X-ray beam 18a–c on each path 20. For the present invention, the relative position of each filter 32, 34, 36; 38 with respect to the other filters 32, 34, 36, 38 is inconsequential. As further shown, a motor 40 having a shaft 42 can be used to rotate the wheel 30 and filters 32, 34, 36, 38 to successively filter each beam 18 four times while the beam 18 travels substantially along a single path 20, with each of the four filtrations occurring with a different filter 32, 34, 36, 38. Accordingly, each time a beam 18 is moved to a new path 20, the wheel 30 is rotated through one complete revolution to once again filter the beam 18 four times. Alternatively, the wheel 30 can be located between the X-ray source 12 and the collimator 16 (this configuration not shown). As shown, a bracket 44 can be used to attach the motor 40 to the X-ray source 12 to allow the wheel 30, the filters 32, 34, 36, 38, the motor 40 and the shaft 42 to travel with the X-ray source 12 as the source 12 moves along the track 28 relative to the object 26. Each time a beam 18 is successively filtered four times, four different electrical signals are produced by a detector 24. For the present invention, a computer processor (not shown) can be configured to manipulate the four electrical signals created for each path 20 to produce an image signal for the path 20. For example, each path 20 can be used to produce an image signal that represents a single pixel in the final image. Or stated another way, a computer process can be configured to subtract, pixel by pixel, the digital images of each pair of the four images obtained with the filtered beam 18. The two digital difference images are further subtracted to finally produce the contrast enhancement image. Once an image signal is established for each desired path 20, conventional tomography techniques known in the pertinent art can be used to combine all the image signals (one image signal for each path 20) into a composite image that shows the internal features of the object 26.

Figure 1:
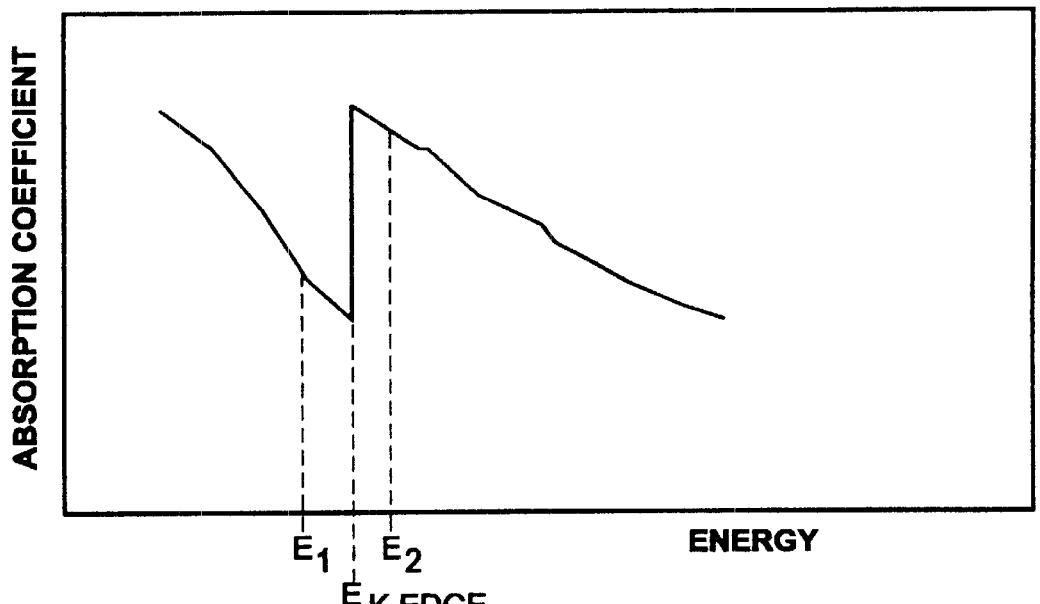
FIG. 1 is a graph showing the variation of absorption coefficient with radiation energy for a typical chemical element.
Figure 3:
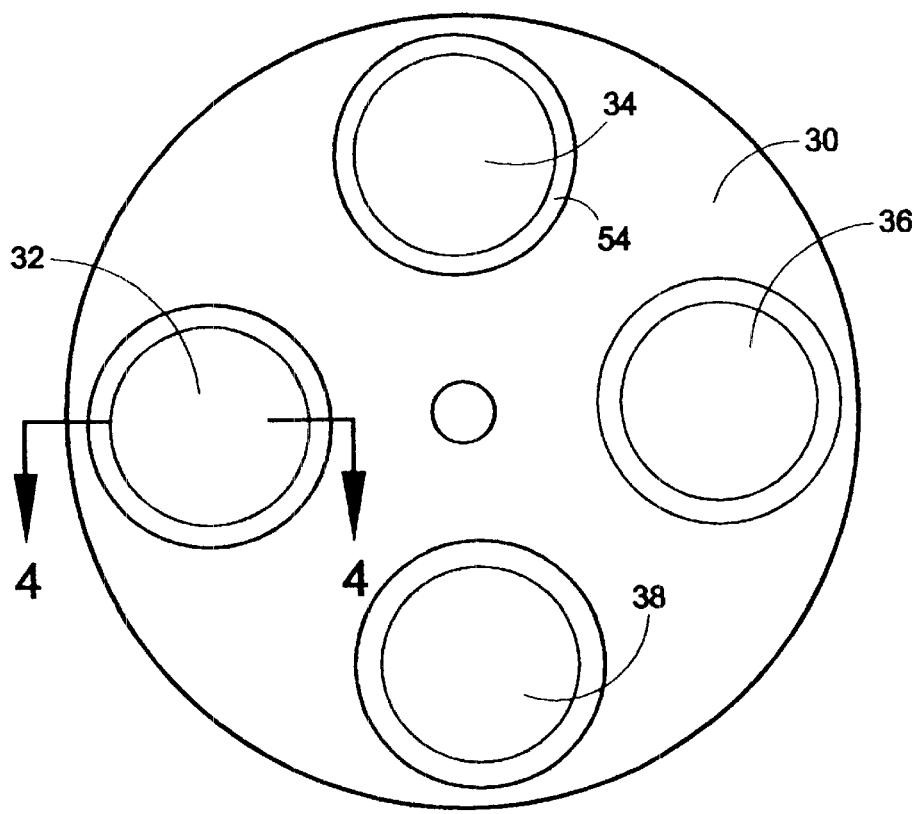
FIG. 3 is an elevational view of a filter set and wheel as seen along line 3—3 in FIG. 2.
Figure 4:
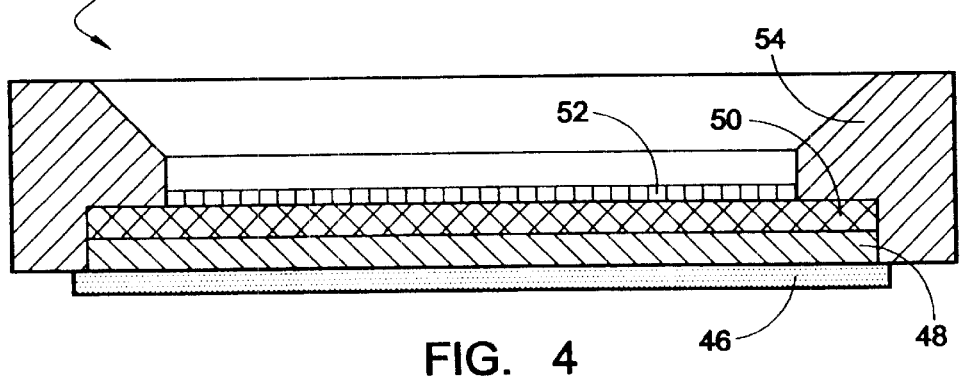
FIG. 4 is a cross-sectional view of a filter and filter holder as seen along line 4—4 in FIG. 3.

Referring now to FIG. 3, a filter set having four different filters 32, 34, 36, 38 is mounted on the wheel 30 to allow each beam 18 on each path 20 to be successively filtered four times. As further detailed below, a unique filter set is designed for use with a specific contrast agent that is prescribed for introduction into the object 26. Specifically, the chemical constituents and thickness of each filter 32, 34, 36, 38 is determined with reference to the specific contrast agent that is being used. FIG. 4 shows an exemplary filter 32 having layers 46, 48, 50 and 52. Specifically, the filter 32 can include an optional transparent layer 46, a filtering layer 48, an optional additional balance layer 50 and an optional protective layer 52. It is to be appreciated that each filter 32, 34, 36, 38 will have different layers 46, 48, 50, 52, the layers 46, 48, 50, 52 differing in both chemical makeup and thickness. For the present invention, the optional transparent layer 46 can be included to support as well as protect the other layers 48, 50, 52. The optional protective layer 52 can be included to protect the other layers 48, 50 from corrosion or other environmental factors. The function of the filtering layer 48 and the additional balance layer 50 are discussed below. As seen by cross-referencing FIGS. 3 and 4, a metal ring 54 can be used to hold the layers 46, 48, 50, 52 together and attach them to the wheel 30.

When used in conjunction with a contrast agent containing a chemical element having a $K_{EDGE,\ CONTRAST\ AGENT}$, a filter set is constructed in accordance with the present invention having a filter 32 with a filtering layer 48 that contains a chemical element having a $K_{EDGE}$ that is greater than $K_{EDGE,\ CONTRAST\ AGENT}$, and a filter 34 with a filtering layer 48 that contains a chemical element having a $K_{EDGE}$ that is greater than or equal to $K_{EDGE,\ CONTRAST\ AGENT}$. Further, the filter set is constructed in accordance with the present invention having a filter 36 with a filtering layer 48 that contains a chemical element having a $K_{EDGE}$ that is less than or equal to $K_{EDGE,\ CONTRAST\ AGENT}$, and a filter 38 with a filtering layer 48 that contains a chemical element having a $K_{EDGE}$ that is less than $K_{EDGE,\ CONTRAST\ AGENT}$. For most contrast agents, both the filter 36 and the filter 38 include a filtering layer 48 that contains the same chemical element that is used in the contrast agent (i.e. a chemical element having a $K_{EDGE,\ CONTRAST\ AGENT}$), but the filtering layer 48 of filter 36 may differ in thickness from the filtering layer 48 of filter 38. The invention includes specific chemical elements and thickness' sufficient to create filter sets for various contrast agents as shown in Table 1.

Referring back to FIG. 2, in the operation of the present invention, a contrast agent is first introduced into the object 26. Once introduced, the contrast agent will be selectively absorbed or localized in specific regions to thereby establish portions of the object 26 having differing concentrations of contrast agent. Table 1, below, lists a number of suitable contrast agents that are either in current use for imaging portions of the human body or are contemplated for future use. It is to be appreciated that conventional methods of administering the contrast agent that are known in the pertinent art can be employed. Further, it is anticipated that the present invention is applicable to the imaging of a non-human object 26, such as a structural component for a machine or device (not shown). In this case, a material in the structural component can be used as a contrast agent and a suitable filter set constructed accordingly.

TABLE 1

Combinations of useable contrast elements and filter elements to be applied to $K_{EDGE}$ subtraction technique for image contrast enhancement

| Contrast Element | Atomic Number Z | $K_{EDGE}$, (CONTRAST AGENT) keV | Filter 32 chemical element and thickness ($\mu$m) | Filter 34 chemical element and thickness ($\mu$m) | Filter 36 chemical element and thickness ($\mu$m) | Filter 38 chemical element and thickness ($\mu$m) |
|---|---|---|---|---|---|---|
| I  | 53 | 33.1694 | $^{55}$Cs 290.0 | $^{53}$I 120.0  | $^{53}$I 450.0   | $^{52}$Te 385.0 |
| Xe | 54 | 34.5616 | $^{56}$Ba 180.0 | $^{55}$Cs 350.0 | $^{53}$I 450.0   | $^{52}$Te 385.0 |
| Cs | 55 | 35.9846 | $^{56}$Ba 180.0 | $^{55}$Cs 350.0 | $^{55}$Cs 1340.0 | $^{53}$I 550.0  |
| Ba | 56 | 37.4406 | $^{57}$La 105.0 | $^{56}$Ba 200.0 | $^{56}$Ba 805.0  | $^{55}$Cs 1575.0|
| Sm | 62 | 46.8342 | $^{63}$Eu 136.0 | $^{62}$Sm 100.0 | $^{62}$Sm 465.0  | $^{60}$Nd 545.0 |
| Eu | 63 | 48.5190 | $^{64}$Gd 120.0 | $^{63}$Eu 185.0 | $^{63}$Eu 690.0  | $^{62}$Sm 500.0 |
| Gd | 64 | 50.2391 | $^{65}$Tb 140.0 | $^{64}$Gd 152.0 | $^{64}$Gd 500.0  | $^{63}$Eu 770.0 |
| Tb | 65 | 51.9957 | $^{66}$Dy 130.0 | $^{65}$Tb 140.0 | $^{65}$Tb 515.0  | $^{64}$Gd 565.0 |
| Dy | 66 | 53.7885 | $^{67}$Ho 130.0 | $^{66}$Dy 140.0 | $^{66}$Dy 540.0  | $^{65}$Tb 582.0 |
| Ho | 67 | 55.6177 | $^{68}$Er 130.0 | $^{67}$Ho 140.0 | $^{67}$Ho 550.0  | $^{66}$Dy 585.0 |
| Er | 68 | 57.4855 | $^{69}$Tm 135.0 | $^{68}$Er 145.0 | $^{68}$Er 550.0  | $^{67}$Ho 600.0 |
| Lu | 71 | 63.3138 | $^{72}$Hf 110.0 | $^{71}$Lu 155.0 | $^{71}$Lu 595.0  | $^{70}$Yb 900.0 |
| Hf | 72 | 65.3508 | $^{73}$Ta 97.0  | $^{72}$Hf 127.0 | $^{72}$Hf 440.0  | $^{71}$Lu 610.0 |
| Ta | 73 | 67.4164 | $^{74}$W 84.0   | $^{73}$Ta 100.0 | $^{73}$Ta 330.0  | $^{72}$Hf 425.0 |
| W  | 74 | 69.5250 | $^{75}$Re 80.0  | $^{74}$W 90.0   | $^{74}$W 330.0   | $^{73}$Ta 396.0 |
| Re | 75 | 71.6764 | $^{76}$Os 80.0  | $^{75}$Re 88.0  | $^{75}$Re 320.0  | $^{74}$W 357.0  |
| Os | 76 | 73.8708 | $^{77}$Ir 80.0  | $^{76}$Os 83.0  | $^{76}$Os 315.0  | $^{75}$Re 346.0 |
| Ir | 77 | 76.1110 | $^{78}$Pt 90.0  | $^{77}$Ir 90.0  | $^{77}$Ir 330.0  | $^{76}$Os 340.0 |
| Bi | 83 | 90.5259 | $^{90}$Th 170.0 | $^{83}$Bi 250.0 | $^{83}$Bi 972.0  | $^{82}$Pb 870.0 |

Once a contrast agent has been introduced, the object 26 can be placed between the X-ray source 12 and the detector array 22 as shown in FIG. 2. Next, the X-ray source 12 is located at a first position and activated to produce one or more beams 18a–c travelling through the object 26 on a first set of paths 20a–c. Next, the wheel 30 containing the filters 32, 34, 36, 38 is rotated to successively interpose each of the four filters 32, 34, 36, 38 between the X-ray source 12 and the object 26 to filter each of the beams 18 with each of the four filters 32, 34, 36, 38. This results in the production of four intensity-proportional signals by a detector 24 for each beam 18. It is to be appreciated that the four signals will be temporally spaced from each other, the spacing corresponding to the time the beam 18 strikes the wheel 30 between adjacent filters 32, 34, 36, 38.

Figure 5A:
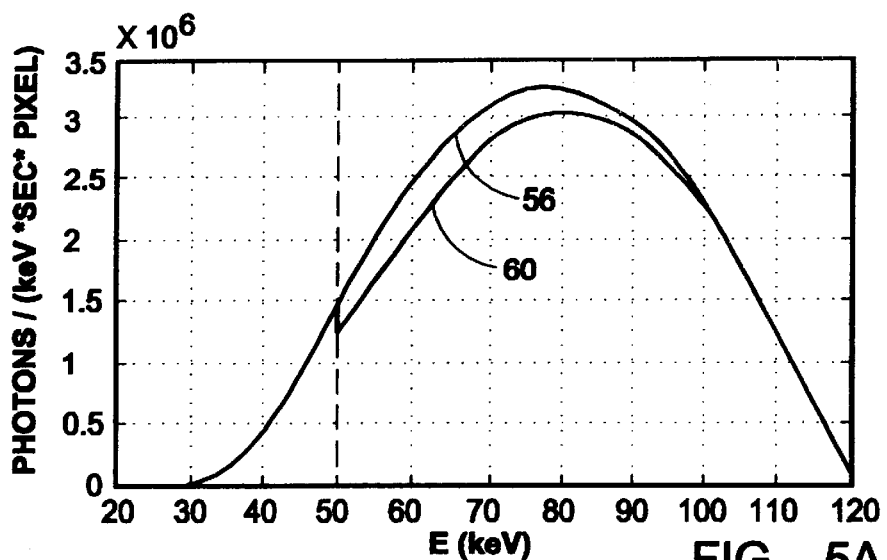
FIG. 5A is a graph showing an exemplary emission spectrum for a conventional X-ray source and a graph showing the spectrum that results after passing the same radiation through a filter having a contrast agent with a $K_{EDGE}$ of approximately 50 keV.
Figure 5B:
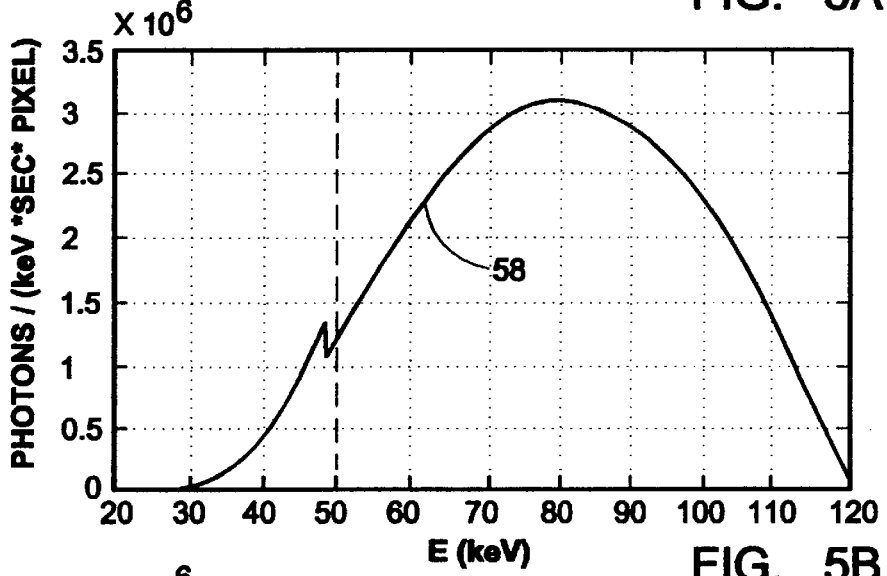
FIG. 5B is a graph showing the spectrum of a beam that results from passing an emission from a conventional X-ray source as shown in FIG. 5A through a filter having a chemical element with a $K_{EDGE}$ of approximately 49 keV.

Referring now to FIG. 5A, a typical emission spectrum for a conventional X-ray source 12 that has passed through a portion of the body having no contrast agent is shown by curve 56. When the spectrum represented by curve 56 reaches a detector 24, an electronic signal that is approximately proportional to the area under curve 56 (the intensity of the emission) is produced. Curve 60 in FIG. 5A represents the spectrum that results after radiation produced by a typical X-ray source 12 is passed through a portion of the body having exemplary contrast agent, Gd, in the absence of filters. Referring now to FIG. 5B, curve 58 represents the spectrum that results after radiation producing curve 56 in FIG. 5A is now passed through filter 38 and a portion of the body having no contrast agent. In this case, filter 38 has a filtering layer 48 having a chemical element with a $K_{EDGE}$ of approximately 49 keV. Accordingly, the electronic signal produced by a detector 24 when filter 38 is interposed between the X-ray source 12 and the detector 24 will be approximately proportional to the area under curve 58. Filter 36, in general, has a filtering layer 48 having the same chemical element that is used in the contrast agent. In this example, filter 36 has a chemical element with a $K_{EDGE,\ CONTRAST\ AGENT}$ of approximately 50 keV. The spectrum received by a detector 24 when filter 36 is interposed between the X-ray source 12 and the detector 24 is approximately represented as curve 60. Accordingly, the signal produced by a detector 24 when filter 36 is interposed between the X-ray source 12 and the detector 24 will be approximately proportional to the area under curve 60.

Figure 6A:
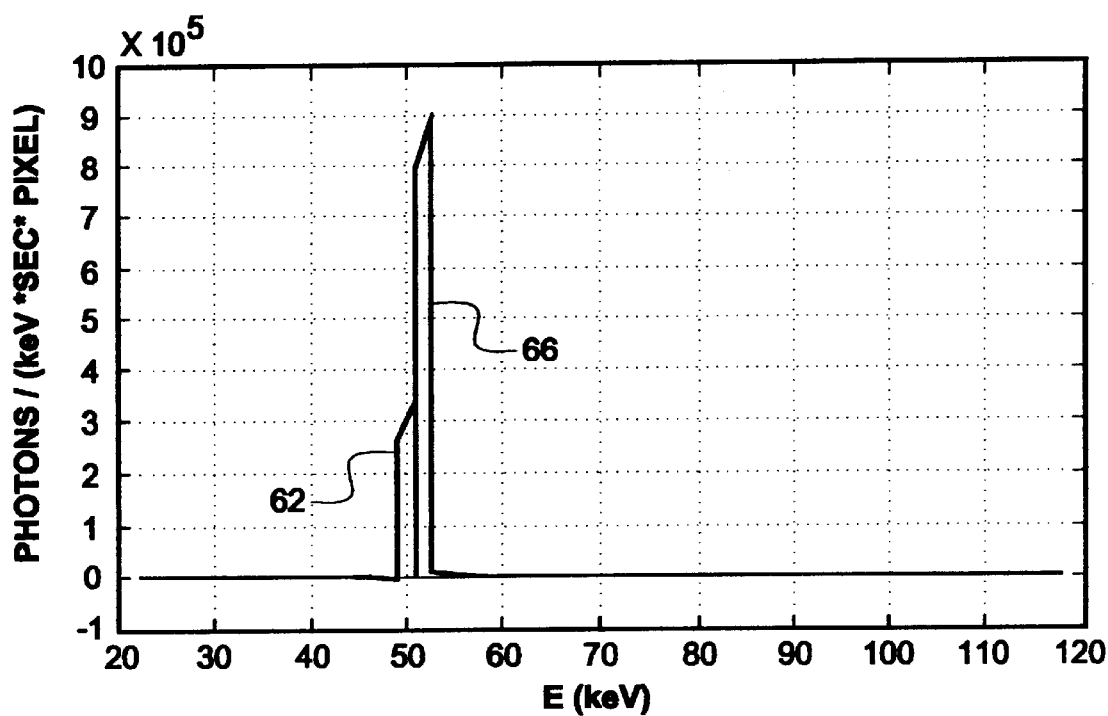
FIG. 6A is a graph showing two quasi-monochromatic radiation signals that are simulated by the filter system and signal processing methods in accordance with the present invention for a portion of an object that does not contain a contrast agent.
Figure 6B:
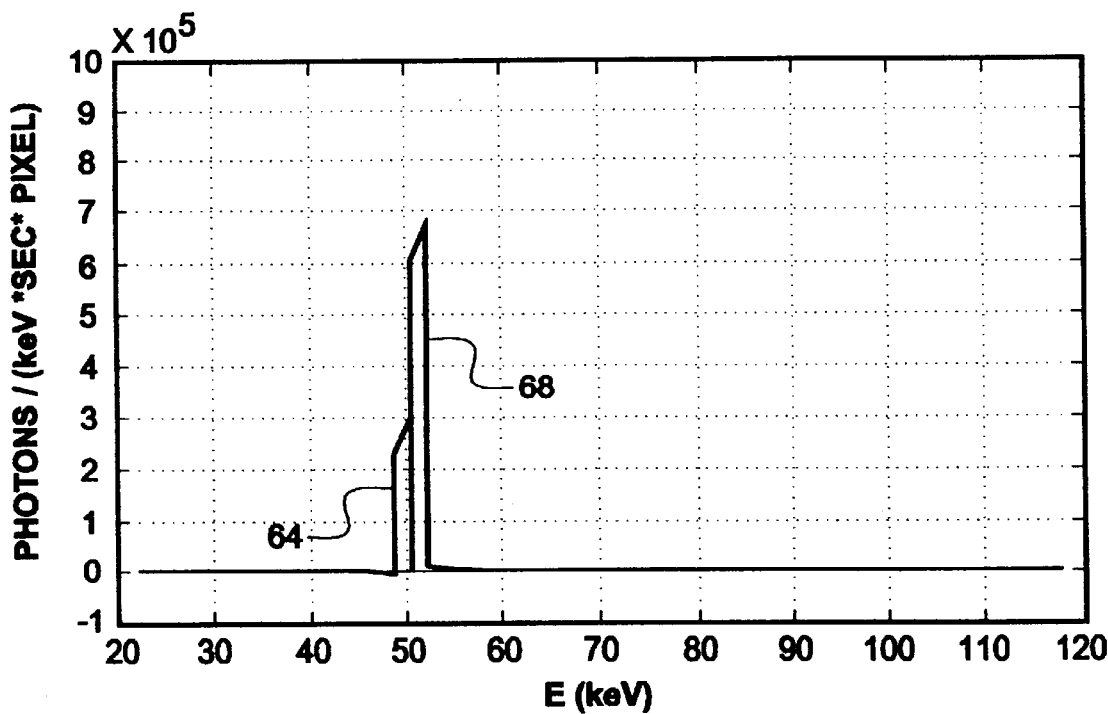
FIG. 6B is a graph showing two quasi-monochromatic radiation signals that are simulated by the filter system and signal processing methods in accordance with the present invention for a portion of the object that contains a contrast agent.

For the present invention, the electrical signal produced by a detector 24 while filter 38 is interposed along a path 20 containing no contrast agent can be subtracted from the electrical signal, after digitization, produced by the detector 24 while the filter 36 is interposed along the same path 20 to produce the second intermediary difference signal. This second intermediary difference signal simulates the image signal that would be obtained if a quasi-monochromatic beam having an average energy slightly below $K_{EDGE,\ CONTRAST\ AGENT}$ were to be passed through the object 26. More specifically, the second intermediary difference signal produced for paths 20 through a portion of the body having no contrast agent simulates the exemplary quasi-monochromatic spectrum shown in FIG. 6A and designated 62. It is to be appreciated that the curve of the quasi-monochromatic spectrum shown in FIG. 6A and designated 62 represents a resultant area obtained by subtracting the area under curve 58 (FIG. 5B) from the area under curve 60 (FIG. 5A). The resultant spectrum is essentially the same as the spectrum when a beam of narrow energy band, or a quasi-monochromatic beam, were used as the source. Similarly, the second intermediary difference signal produced for paths 20 through a portion of the body having a contrast agent simulates the quasi-monochromatic spectrum shown in FIG. 6B and designated 64.

Figure 5C:
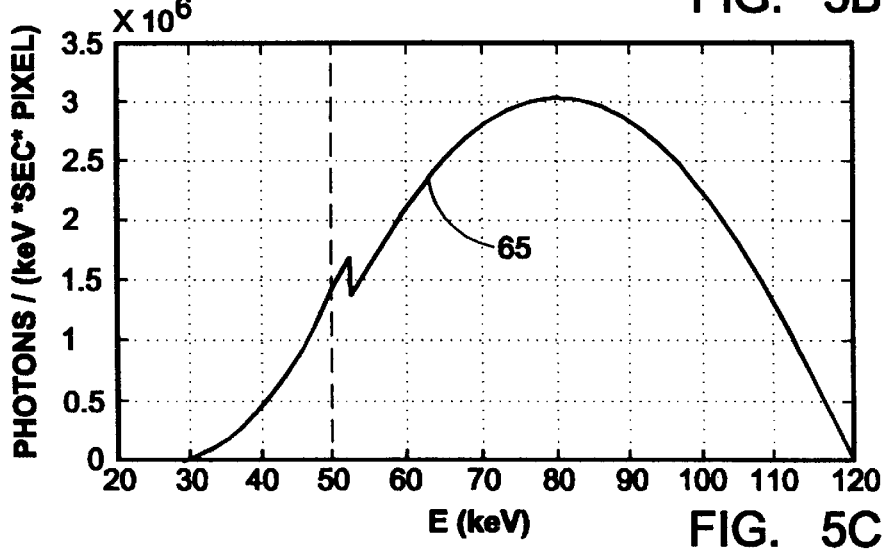
FIG. 5C is a graph showing the spectrum of a beam that results from passing an emission from a conventional X-ray source as shown in FIG. 5A through a filter having a chemical element with a $K_{EDGE}$ of approximately 51 keV.

In a similar fashion, the processor subtracts the digital signal produced by the detector 24 with the filter 34 interposed along the path 20 from the digital signal produced by the detector 24 with the filter 32 interposed along the path 20 to produce a first intermediary difference signal. A curve representing the spectrum that results after radiation producing curve 56 in FIG. 5A is now passed through filter 32 and a portion of the body having no contrast agent is shown in FIG. 5C and designated curve 65. It is to be appreciated that the first intermediary difference signal simulates the image signal that would be obtained if a quasi-monochromatic beam having an average energy slightly above $K_{EDGE,\ CONTRAST\ AGENT}$ were to be passed through the object 26. More specifically, the first intermediary difference signal produced for paths 20 having no contrast agent simulates the exemplary quasi-monochromatic spectrum shown in FIG. 6A and designated 66. Similarly, the first intermediary difference signal produced for paths 20 having contrast agent simulates the exemplary quasi-monochromatic spectrum shown in FIG. 6B and designated 68.

Next, the processor subtracts the second intermediary difference signal from the first intermediary difference signal to produce an image signal for the path 20. More specifically, the image signal produced for paths 20 having no contrast agent simulates the difference in intensity between spectrum curve 66 and spectrum curve 62 in FIG. 6A. Similarly, the image signal produced for paths 20 having a contrast agent simulates the difference in intensity between spectrum curve 68 and spectrum curve 64 in FIG. 6B. This final difference is the data to be processed for tomography or angiography. The final difference signal strongly varies with concentration and thickness of the contrast element due to the variation of absorption. This results in an enhanced contrast image between the region with the contrast agent and the region without.

Figure 7:
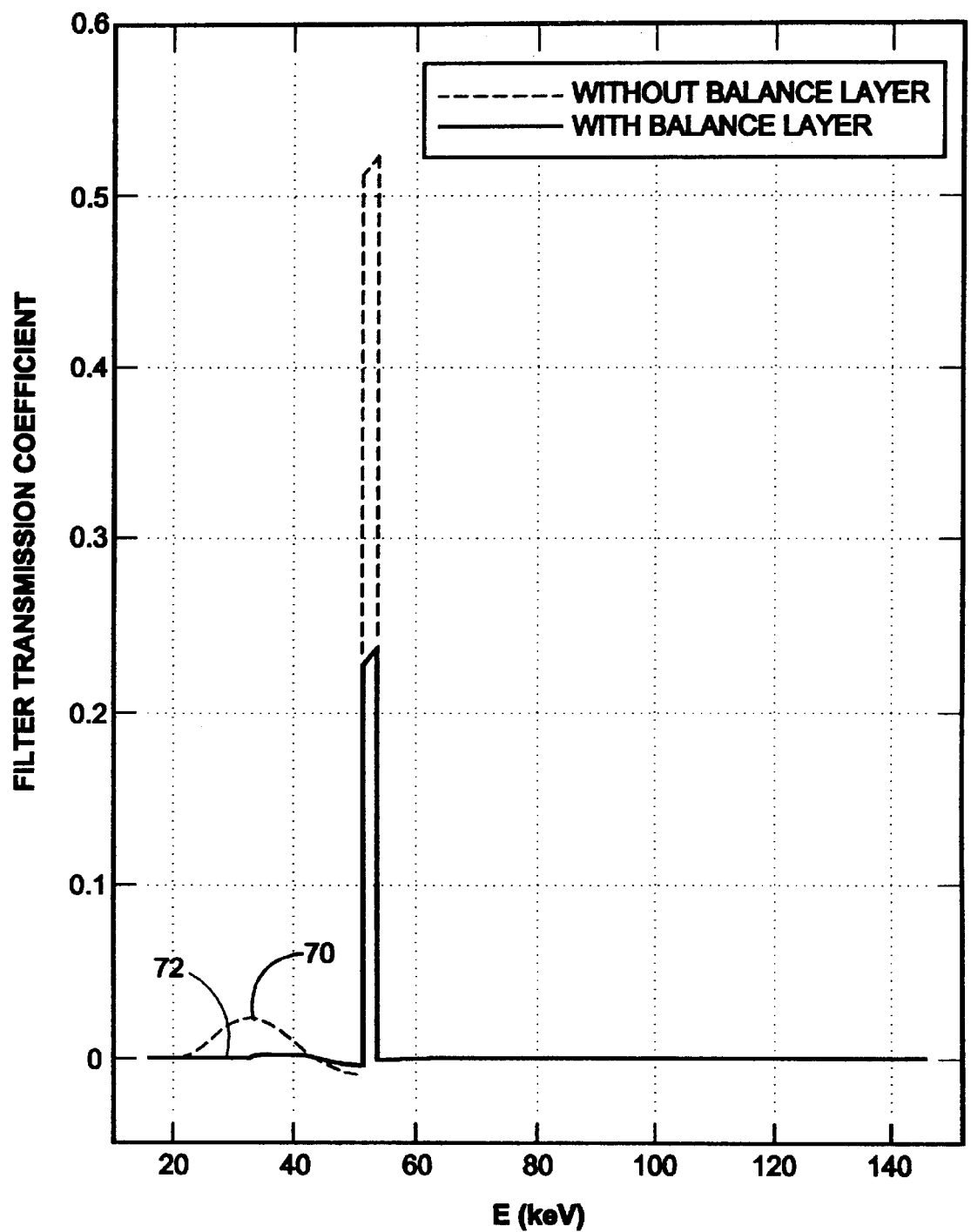
FIG. 7 is a graph showing the performance effect achieved when an additional balance layer is incorporated in a filter.

Referring now to FIG. 7, the effect of additional balance layers 50 in a filter set is shown. Specifically, FIG. 7 compares the quasi-monochromatic signal that is simulated without additional balance layers 50 (curve 70) and the quasi-monochromatic signal that is simulated with additional balance layers 50 (curve 72). The curve 72 was generated for a filter set having a filter 32 with a filtering layer 48 that includes 140.0 μm of $^{65}$Tb and an additional balance layer 50 of 260.0 μm of $^{65}$Tb and a filter 34 that includes 152.0 μm of $^{64}$Gd and an additional balance layer 50 of 260.0 μm of $^{65}$Tb. With cross reference to Table 1 and FIG. 7, these two filters 32, 34 can be used in a filter set in conjunction with the contrast agent Gd to generate the first intermediary difference signal. As shown in FIG. 7, the use of additional balance layers 50 reduces the non-zero difference of the filter transmission outside the energy pass band. Of course, this effect is obtained by paying the price of reducing the radiation intensity within the pass band (by a factor of about two, in this case). In practice, the additional balance layer 50 is designed to provide a compromise between the enhancement of the quality of monochromatization (i.e. a thicker additional balance layer 50 providing better balance) and the intensity level within the energy pass band (i.e. a larger number of photons to provide a better Signal-To-Noise ratio).

Referring back to FIG. 2, once image signals are obtained for the first set of paths 20a–c, the X-ray source 12 and collimator 16 can be moved to a second position (shown by dashed lines) to cause the beams 18a–c emanating from the collimator 16 to travel along a new set of paths 20d–f. While the X-ray source 12 and collimator 16 are at the second position, the wheel 30 is again rotated to successively interpose each of the four filters 32, 34, 36, 38 between the X-ray source 12 and the object 26 to again filter each of the beams 18a–c with each of the four filters 32, 34, 36, 38. Again, four intensity-proportional signals are produced by a detector 24 for each beam 18. For the present invention, these four signals can be manipulated by a processor (not shown) to produce an image signal for each new path 20d–f. This process of moving the X-ray source 12 and producing an image signal for each new path 20 can be repeated as desired. Further, it is to be appreciated that the X-ray source 12 can be moved continuously around the object 26. When this technique is used, the wheel 30 containing the filters 32, 34, 36, 38 can be rotated continuously as the X-ray source 12 moves. By rotating the wheel 30 very rapidly, each beam 18 can be filtered four times before significant movement of the beam 18 occurs. Thus, in effect, each beam 18 remains on a single path 20 while the successive filtration takes place. Once an image signal is produced for all paths 20 of interest, conventional tomography techniques can be used to combine all the image signals (one image signal for each path 20) into a composite image that shows the internal features of the object 26.

While the particular imaging systems and methods as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A system for creating an image of an object that contains a contrast agent including a chemical element having a $K_{EDGE,\ CONTRAST\ AGENT}$, said system comprising:
   an X-ray source configured to emit an X-ray beam having a spectrum of X-ray radiation, said X-ray source configured to emit said beam along a fixed direction relative to said X-ray source;
   means for moving said X-ray source to cause said beam to move;
   a detector positioned to interpose said object between said detector and said X-ray source, said detector for receiving radiation and producing electrical current that is proportional to the intensity of the radiation received;
   a first filter having a chemical element with a $K_{EDGE}$ greater than $K_{EDGE,\ CONTRAST\ AGENT}$ and a second filter having a chemical element with a $K_{EDGE}$ in an inclusive range between $K_{EDGE\ CONTRAST\ AGENT}$ and a value less than $K_{EDGE,\ CONTRAST\ AGENT}$, said first and second filter chemical elements having respective thicknesses for producing respective filtered radiation signals that can be processed to simulate quasi-monochromatic radiation having an average energy greater than $K_{EDGE,\ CONTRAST\ AGENT}$;
   a third filter having a chemical element with a $K_{EDGE}$ in an inclusive range between $K_{EDGE\ CONTRAST\ AGENT}$ and a value greater than $K_{EDGE,\ CONTRAST\ AGENT}$ and a fourth filter having a chemical element with a $K_{EDGE}$ less than $K_{EDGE,\ CONTRAST\ AGENT}$, said third and fourth filter chemical elements having respective thicknesses for producing respective filtered radiation signals that can be processed to simulate guasi-monochromatic radiation having an average energy less than $K_{EDGE,\ CONTRAST\ AGENT}$;
   a means for mounting said first, second, third and fourth filters on said X-ray source and for successively positioning each said filter into contact with said beam to filter said beam, said mounting means to cause said filters to move with said X-ray source; and
   a processor connected to said detector for producing an image of said object from said electrical current.

2. A system as recited in claim 1 further comprising a means for moving said detector to allow said detector to maintain a continuous angular orientation with respect to said X-ray source as said X-ray source moves.

3. A system as recited in claim 1 wherein said processor is configured to subtract said electrical current produced by said detector while said second filter is in contact with said beam from said electrical current produced by said detector while said first filter is in contact with said beam to produce a first intermediary: difference signal said processor being further configured to subtract said electrical current produced by said detector while said fourth filter is in contact with said beam from said electrical current produced by said detector while said third filter is in contact with said beam to produce a second intermediary difference signal; and wherein said processor is configured to subtract said second intermediary difference signal from said first intermediary difference signal to produce an image signal.

4. A system for creating an image of an object that contains a contrast agent including a chemical element having a $K_{EDGE,\ CONTRAST\ AGENT}$, said system comprising:
   a means for directing a spectrum of electromagnetic radiation onto a plurality of paths, each said path extending through said object;
   a first filter having a chemical element with a $K_{EDGE}$ greater than $K_{EDGE,\ CONTRAST\ AGENT}$ and a second filter having a chemical element with a $K_{EDGE}$ in an inclusive range between $K_{EDGE\ CONTRAST\ AGENT}$ and a value less than $K_{EDGE,\ CONTRAST\ AGENT}$, said first and second filter chemical elements having respective thicknesses for producing respective filtered radiation signals that can be processed to simulate quasi-monochromatic radiation having an average energy greater than $K_{EDGE,\ CONTRAST\ AGENT}$;
   a third filter having a chemical element with a $K_{EDGE}$ in an inclusive range between $K_{EDGE\ CONTRAST\ AGENT}$ and a value greater than $K_{EDGE,\ CONTRAST\ AGENT}$ and a fourth filter having a chemical element with a $K_{EDGE}$ less than $K_{EDGE,\ CONTRAST\ AGENT}$, said third and fourth filter chemical elements having respective thicknesses for producing respective filtered radiation signals that can be processed to simulate quasi-monochromatic radiation having an average energy less than $K_{EDGE,\ CONTRAST\ AGENT}$;
   a means for successively interposing each said filter on each said path to create a plurality of filtered radiation signals for each said path;
   a means for receiving said filtered radiation signals for each said path, and producing an electrical signal for each said filtered radiation signal received, each said electrical signal being proportional to the intensity of radiation received; and
   a processor for operation on said electrical signals to produce an image of said object.

5. A system as recited in claim 4 wherein said means for directing a spectrum of electromagnetic radiation onto a plurality of paths comprises:
   a radiation source configured to emit radiation in at least one direction; and
   a means for moving said radiation source to cause said source to successively emit said radiation in a plurality of directions.

6. A systems recited in claim 5 wherein said means for receiving said filtered radiation signals for each said path comprises:
   at least one radiation detector, each said radiation detector oriented to detect radiation, in at least one direction; and
   a means for moving each said radiation detector to cause each said radiation detector to successively detect radiation in a plurality of directions.

7. A system as recited in claim 4 wherein said interposing means is positioned to successively interpose each said filter on each said path before said radiation passes through said object.

8. A system as recited in claim 4 wherein said means for successively interposing each said filter on each said path comprises:
   a wheel defining an axis and formed with a plurality of holes, each said hole for accommodating a said filter; and means for selectively rotating said wheel about said axis.

9. A system as recited in claim 5 wherein said means for successively interposing each said filter of a said filter set on each said path comprises:
  a wheel defining an axis and formed with a plurality of holes, each said hole for accommodating a said filter; and
  means for selectively rotating said wheel about said axis, said means mounted on said radiation source to cause said rotating means and said wheel to move with said radiation source.

10. A system as recited in claim 4 wherein said processor is configured to subtract said electrical signal produced with said second filter interposed along a first path from said electrical signal produced with said first filter interposed along a said first path to produce a first intermediary difference signal; said processor being further configured to subtract said electrical signal produced with said fourth filter interposed along said first path from said electrical signal produced with said third filter interposed along first path to produce a second intermediary difference signal; and said processor is configured to subtract said second intermediary difference signal from said first intermediary difference signal to produce an image signal for said first path.

11. A system as recited in claim 4 wherein said contrast agent comprises the chemical element iodine, said first filter comprises the chemical element Cs at a thickness of about 290.0 µm and said second filter comprises chemical element I at a thickness of about 120.0 µm, said third filter comprises the chemical element I at a thickness of about 450.0 µm and said fourth filter comprises the chemical element Te at a thickness of about 385.0 µm.

12. A system as recited in claim 4 wherein said contrast agent comprises the chemical element Xe, said first filter comprises the chemical element Ba at a thickness of about 180.0 µm and said second filter comprises the chemical element Cs at a thickness of about 350.0 µm, said third filter comprises the chemical element I at a thickness of about 450.0 µm and said fourth filter comprises the chemical element Te at a thickness of about 385.0 µm.

13. A system as recited in claim 4 wherein said contrast agent comprises the chemical element Cs, said first filter comprises the chemical element Ba at a thickness of about 180.0 µm and said second filter comprises the chemical element Cs at a thickness of about 350.0 µm, said third filter comprises the chemical element Cs at a thickness of about 1340.0 µm and said fourth filter comprises the chemical element I at a thickness of about 550.0 µm.

14. A system as recited in claim 4 wherein said contrast agent comprises the chemical element Ba, said first filter comprises the chemical element La at a thickness of about 105.0 µm and said second filter comprises the chemical element Ba at a thickness of about 200.0 µm, said third filter comprises the chemical element Ba at a thickness of about 805.0 µm and said fourth filter comprises the chemical element Cs at a thickness of about 1575.0 µm.

15. A system as recited in claim 4 wherein said contrast agent; comprises the chemical element Sm, said first filter comprises the chemical element Eu at a thickness of about 136.0 µm and said second filter comprises the chemical element Sm at a thickness of about 100.0 µm, said third filter comprises the chemical element Sm at a thickness of about 465.0 µm and said fourth filter comprises the chemical element Nd at a thickness of about 545.0 µm.

16. A system as recited in claim 4 wherein said contrast agent comprises the chemical element Eu, said first filter comprises the chemical element Gd at a thickness of about 120.0 µm and said second filter comprises the chemical element Eu at a thickness of about 185.0 µm, said third filter comprises the chemical element Eu at a thickness of about 690.0 µm, and said fourth filter comprises the chemical element Sm at a thickness of about 500.0 µm.

17. A system as recited in claim 4 wherein said contrast agent comprises the chemical element Gd, said first filter comprises the chemical element Tb at a thickness of about 140.0 µm and said second filter comprises the chemical element Gd at a thickness of about 152.0 µm, said third filter comprises the chemical element Gd at a thickness of about 500.0 µm and said fourth filter, filter comprises the chemical element Eu at a thickness of about 770.0 µm.

18. A system as recited in claim 4 wherein said contrast agent comprises the chemical element Tb, said first filter comprises the chemical element Dy at a thickness of about 130.0 µm and said second filter comprises the chemical element Tb at a thickness of about 140.0 µm, said third filter comprises the chemical element Tb at a thickness of about 515.0 µm and said fourth filter comprises the chemical element Gd at a thickness of about 565.0 µm.

19. A system as recited in claim 4 wherein said contrast agent comprises the chemical element Dy, said first filter comprises the chemical element Ho at a thickness of about 130.0 µm and said second filter comprises the chemical element Dy at a thickness of about 140.0 µm, said third filter comprises the chemical element Dy at a thickness of about 540.0 µm and said fourth filter comprises the chemical element Tb at a thickness of about 582.0 µm.

20. A system as recited in claim 4 wherein said contrast agent comprises the chemical element Ho, said first filter comprises the chemical element Er at a thickness of about 130.0 µm and said second filter comprises the chemical element Ho at a thickness of about 140.0 µm, said third filter comprises the chemical element Ho at a thickness of about 550.0 µm and said fourth filter comprises the chemical element Dy at a thickness of about 585.0 µm.

21. A system as recited in claim 4 wherein said contrast agent comprises the chemical element Er, said first filter comprises the chemical element Tm at a thickness of about 135.0 µm and said second filter comprises the chemical element Er at a thickness of about 145.0 µm, said third filter comprises the chemical element Er at a thickness of about 550.0 µm and said fourth filter comprises the chemical element Ho at a thickness of about 600.0 µm.

22. A system as recited in claim 4 wherein said contrast agent comprises the chemical element Lu, said first filter comprises the chemical element Hf at a thickness of about 110.0 µm and said second filter comprises the chemical element Lu at a thickness of about 155.0 µm, said third filter comprises the chemical element Lu at a thickness of about 595.0 µm and said fourth filter comprises the chemical element Yb at a thickness of about 900.0 µm.

23. A system as recited in claim 4 wherein said contrast agent comprises the chemical element Hf, said first filter comprises the chemical element Ta at a thickness of about 97.0 µm and said second filter comprises the chemical element Hf at a thickness of about 127.0 µm, said third filter comprises the chemical element Hf at a thickness of about 440.0 µm and said fourth filter comprises the chemical element Lu at a thickness of about 610.0 µm.

24. A system as recited in claim 4 wherein said contrast agent comprises the chemical element Ta, said first filter comprises the chemical element W at a thickness of about 84.0 µm and said second filter comprises the chemical element Ta at a thickness of about 100.0 µm, said third filter comprises the chemical element Ta at a thickness of about 330.0 µm and said fourth filter comprises the chemical element Hf at a thickness of about 425.0 µm.

25. A system as recited in claim 4 wherein said contrast agent comprises the chemical element W, said first filter comprises the chemical element Re at a thickness of about 80.0 µm and said second filter comprises the chemical element W at a thickness of about 90.0 µm, said third filter comprises the chemical element W at a thickness of about 330.0 µm and said fourth filter comprises the chemical element Ta at a thickness bf about 396.0 µm.

26. A system as recited in claim 4 wherein said contrast agent comprises the chemical element Re, said first filter comprises the chemical element Os at a thickness of about 80.0 µm and said second filter comprises the chemical element Re at a thickness of about 88.0 µm, said third filter comprises the chemical element Re at a thickness of about 320.0 µm and said fourth filter comprises the chemical element W at a thickness of about 357.0 µm.

27. A system as recited in claim 4 5wherein said contrast agent comprises the chemical element Os, said first filter comprises the chemical element Ir at a thickness of about 80.0 µm and said second filter comprises the chemical element Os at a thickness of about 83.0 µm, said third filter comprises the chemical element Os at a thickness of about 315.0 µm and said fourth filter comprises the chemical element Re at a thickness of about 346.0 µm.

28. A system as recited in claim 4 wherein said contrast agent comprises the chemical element Ir, said first filter comprises the chemical element Pt at a thickness of about 90.0 µm and said second filter comprises the chemical element Ir at a thickness of about 90.0 µm, said third filter comprises the chemical element Ir at a thickness of about 330.0 µm and said fourth filter comprises the chemical element Os at a thickness of about 340.0 µm.

29. A system as recited in claim 4 wherein said contrast agent comprises the chemical element Bi, said first filter comprises the chemical element Th at a thickness of about 170.0 µm and said second filter comprises the chemical element Bi at a thickness of about 250.0 µm, said third filter comprises the chemical element Bi at a thickness of about 972.0 µm and said fourth filter comprises the chemical element Pb at a thickness of about 870.0 µm.

30. A method for creating an image comprising the steps of:

providing an object that contains a contrast agent having a chemical element with $K_{EDGE,\ CONTRAST\ AGENT}$;

directing a spectrum of electromagnetic radiation onto a plurality of paths, each said path extending through said object;

providing a first filter having a chemical element with a $K_{EDGE}$ greater than $K_{EDGE,\ CONTRAST\ AGENT}$;

providing a second filter having a chemical element with a $K_{EDGE}$ in an inclusive range between $K_{EDGE,\ CONTRAST\ AGENT}$ and a value less ta $K_{EDGE,\ CONTRAST\ AGENT}$, said first and second filter chemical elements having respective thicknesses for producing respective filtered radiation signals that can be processed to simulate guasi-monochromatic radiation having an average energy greater than $K_{EDGE,\ CONTRAST\ AGENT}$;

providing a third filter having a chemical element with a $K_{EDGE}$ in an inclusive range between $K_{EDGE,\ CONTRAST\ AGENT}$ and a value greater than $K_{EDGE,\ CONTRAST\ AGENT}$;

providing a fourth filter having a chemical element with a $K_{EDGE}$ less than $K_{EDGE,\ CONTRAST\ AGENT}$, said third and fourth filter chemical elements having respective thicknesses for producing respective filtered radiation signals that can be Processed to simulate quasi-monochromatic radiation having an average energy less than $K_{EDGE,\ CONTRAST\ AGENT}$;

successively interposing each said filter of one:said filter set on each said path to create a plurality of filtered radiation signals for each said path;

receiving said filtered radiation signals for each said path and producing an electrical signal for each said filtered radiation signal received, each said electrical signal being proportional to the intensity of radiation received; and processing said electrical signals to produce an image of said object.

31. A method as recited in claim 30 further comprising the step of administering a said contrast agent into said object.

32. A method as recited in claim 30 wherein said object is a human body.

* * * * *